United States Patent
Sauter et al.

(10) Patent No.: US 6,669,739 B2
(45) Date of Patent: Dec. 30, 2003

(54) AGENT FOR COLORING FIBERS AND METHOD FOR TEMPORARILY COLORING FIBERS

(75) Inventors: Guido Sauter, Marly (CH); Hans-Juergen Braun, Ueberstorf (CH); Nadia Reichlin, Cugy (CH)

(73) Assignee: Wella Aktiengesellschaft, Darmstadt (DE)

( * ) Notice: Subject to any disclaimer, the term of this patent is extended or adjusted under 35 U.S.C. 154(b) by 172 days.

(21) Appl. No.: 10/019,421

(22) PCT Filed: Mar. 9, 2001

(86) PCT No.: PCT/EP01/02685
§ 371 (c)(1),
(2), (4) Date: Dec. 21, 2001

(87) PCT Pub. No.: WO01/86057
PCT Pub. Date: Nov. 15, 2001

(65) Prior Publication Data
US 2002/0172651 A1 Nov. 21, 2002

(30) Foreign Application Priority Data
May 10, 2000 (DE) .......................... 100 22 744

(51) Int. Cl.$^7$ .................................. A61K 7/13
(52) U.S. Cl. ................ 8/405; 8/409; 8/424; 8/426; 8/454; 8/462; 8/565; 8/657; 8/659; 548/511; 548/455
(58) Field of Search .......................... 8/405, 409, 424, 8/426, 454, 462, 565, 657, 659; 548/455, 511

(56) References Cited

U.S. PATENT DOCUMENTS 4,542,224 A * 9/1985 Raue et al. .................. 548/455

FOREIGN PATENT DOCUMENTS

| DE | 197 17 280 A1 | 10/1998 |
|---|---|---|
| DE | 197 17 281 A1 | 10/1998 |
| DE | 299 08 464 U1 | 9/1999 |
| EP | 0 270 972 A | 6/1988 |
| GB | 1 528 590 A | 10/1978 |

OTHER PUBLICATIONS

Houben–Weyl: "Methoden Der Organischen chemie", Band 7, Teil 1, PP. 453–460, 1954.
Jerry March: "Advanced Organic Chemistry", 4–th Edition (1992), PP. 896–898.

* cited by examiner

Primary Examiner—Yogendra N. Gupta
Assistant Examiner—Eisa Elhilo
(74) Attorney, Agent, or Firm—Michael J. Striker

(57) ABSTRACT

The object of the present invention is a preparation for coloring fibers, which is prepared before use by mixing an acidic component (A1), containing at least one enamine of Formula (I)/(Ia) with a component (A2), containing a Schiff's base of Formula (II)

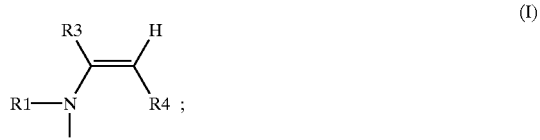

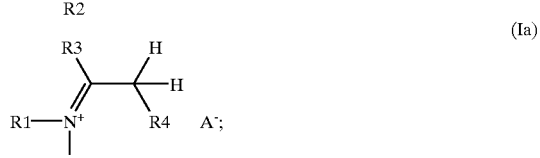

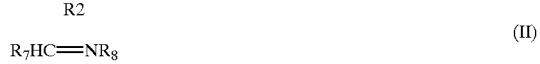

as well as a method for temporarily coloring fibers, for which the coloration, obtained with the aforementioned coloring agent, can be removed once again at any time by a sulfite-containing decolorizing agent.

10 Claims, No Drawings

AGENT FOR COLORING FIBERS AND METHOD FOR TEMPORARILY COLORING FIBERS

The object of the present invention is a preparation for coloring fibers, especially of human hair, which contains enamines and Schiff's bases, it also being possible, if so desired, to decolorize the coloring obtained gently at any later time.

Coloring preparations are divided into the areas of oxidation dyeing agents or of tints, depending on the original color of the hair, which is to be colored, and the desired end result. Oxidation hair dyes are outstandingly suitable for covering higher proportions of gray. The oxidation dyeing agents, which are used for gray portions up to 50%, usually are referred to as oxidative tints. On the other hand, the oxidation dyeing agents, which are used when the proportion of gray exceeds 50% or for "lightening" the color, usually are referred to as so-called oxidative dyes. Direct dyes are mainly contained in non-oxidative dyeing agents (so-called tinting agents). Because of their small size, some direct dyes, such as nitro dyes, can penetrate into the hair and dye it directly, at least in the outer regions. Such tints are very gentle to the hair and usually withstand 6 to 8 washings and enable up to about 20% gray to be covered.

In general, direct and oxidative tints are washed out when the hair is washed a few times. Among other factors, the period depends greatly on the structure of the hair and on the shade used. In some cases, oxidative dyes can fade over time. Usually, however, they remain in the hair until the next time the hair is cut. However, a hair coloring, which can be removed at any time, may be desirable for persons who wish to have a particular color only for a certain time or do not like the coloring achieved. Likewise, in the event that the hair is colored for the first time, the possibility of removing the coloring gently and completely reduces the fear of a too drastic change in color ("test coloring").

The German Offenlegungsschriften 197 17 280 and 197 17 281 disclose the use of a combination of certain heterocyclic carbonyl compounds or benzylidene ketones with amines and/or hydroxy compounds and/or acidic CH compounds for coloring hair without the addition of oxidizing agents. Likewise, the German utility patent 299 08 464 discloses that hair can be dyed permanently by a combination of certain 1,2,3,3-tetramethyl-3H-indolium salts and carbonyl compounds even without the addition of oxidizing agents.

There is however a great need for dyeing agents, which make intensive as well as gentle colorings possible under mild conditions and, if desired, can be decolorize once again at a later time.

It is therefore an object of the present invention, to provide a dyeing agent, which has a very long shelf life and makes possible, on the one hand, a gentle, intensive and stable coloring of the fibers in the yellow, brown, green and violet areas with good fastness properties (wash fastness, crocking fastness, etc.) and, on the other, a gentle and complete removal of this coloring at any time.

Surprisingly, it has now been found that this objective can be accomplished by the use a dyeing agent, which is obtained by mixing two components, the first component containing at least one enamine of Formula (I) or its acid addition salt of Formula (Ia) and the second component containing at least one Schiff's base of Formula (II).

An object of the present invention therefore is a preparation for coloring fibers (A), such as wool, silk, cotton or hair and especially human hair, which is produced by mixing two components (A1) and (A2), wherein the component (A1) has an acidic pH and contains at least one enamine of Formula (I) or its acid addition salt of Formula (Ia)

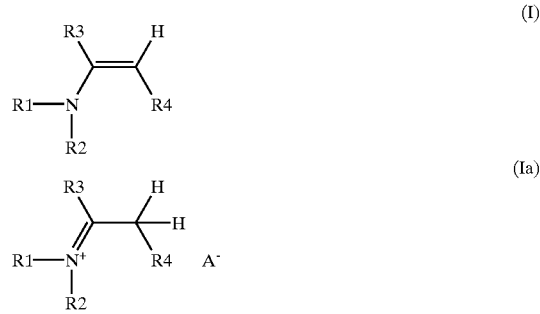

wherein R1 represents a single ring or multi-ring aromatic group, especially an unsubstituted 5-membered or 6-membered aryl group (preferably a phenyl group or naphthyl group), an unsubstituted 5-membered or 6-membered heterocyclic group (preferably a pyridyl group), a 5-membered or 6-membered aryl group, substituted with a C1 to C4 alkyl group, a C1 to C4 hydroxyalkyl group, a hydroxy group, a methoxy group, substituted with a dialkylamino group or a halogen group (F, Cl, Br, I) (preferably a substituted phenyl group), or a 5-membered or 6-membered heterocyclic group, substituted with a C1 to C4 alkyl group, a C1 to C4 hydroxyalkyl group, a hydroxy group, a methoxy group, a dialkylamino group or a halogen group (F, Cl, Br, I) (preferably a substituted pyridyl group or naphthyl group), R2 is a linear or branched C1 to C8 alkyl group, a linear or branched C1 to C8 hydroxyalkyl group or a C1 to C8 alkoxyalkyl group, wherein oxygen atoms may be located between the carbon atoms of the alkyl chain, R3 is a linear or branched C1 to C8 alkyl group, a C1 to C8 alkoxyalkyl group, a linear or branched C1 to C8 alkylene group, a C1 to C8 alkoxyalkylene group, an oxygen atom, a sulfur atom, an —NH group, or an —NR group, wherein R is an alkyl group, an alkoxyalkyl group, a hydroxyalkyl group or hydrogen, the R1 and R3 groups, together with the nitrogen atom and the carbon atom of the basic enamine structure being able to form a cyclic compound and R4 being hydrogen, a linear C1 to C4 alkyl group or a branched C1 to C4 alkyl group, A⁻ being the anion of an organic or inorganic acid, and the component (A2) having an alkaline pH and containing at least one Schiff's base of Formula (II)

wherein R7 is a group of the following formulas

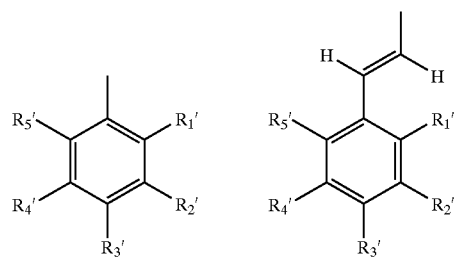

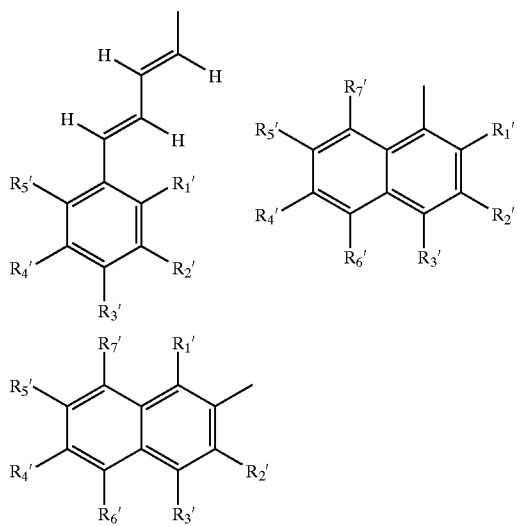

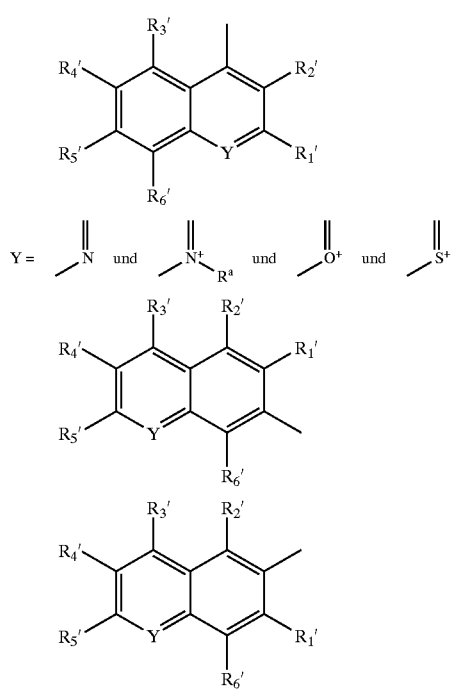

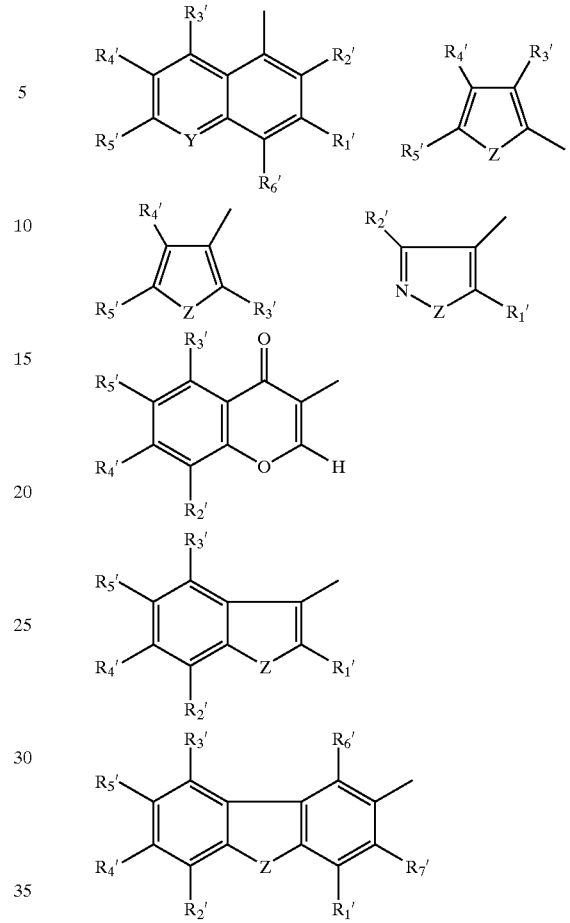

wherein Y and Z in each case are an oxygen atom, a sulfur atom or an NR$^a$ group, R1', R2', R3', R4', R5', R6' and R7' independently of one another are a hydrogen atom, a hydroxyl group, a methoxy group, an aryl group, a halogen atom (F, Cl, Br, I), a —CHO group, a —COR$^a$ group, a —CO$_2$R$^a$ group, an —NO$_2$ group, an —OCOR$^a$ group, an —OCH$_2$ aryl group, an —NH$_2$ group, an —NH$_3^+$ group, an —NHR$^a$ group, an —NR$^a$H$_2^+$ group, an —N(R$^a$)$_2$ group, an —N(R$^a$)$_3^+$ group, an —NHCOR$^a$ group, an —NHCOOR$^a$ group, in which R$^a$ represents a hydrogen atom, a linear or branched C1 to C4 alkyl group, an optionally substituted aromatic carbon ring or heterocyclic ring, with the proviso that at least one of the R1' to R7' groups is not hydrogen, and R8 is a group of the following formulas

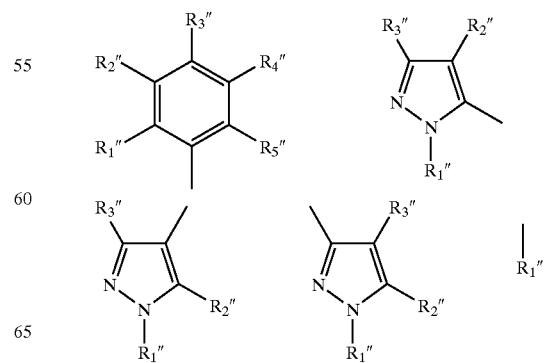

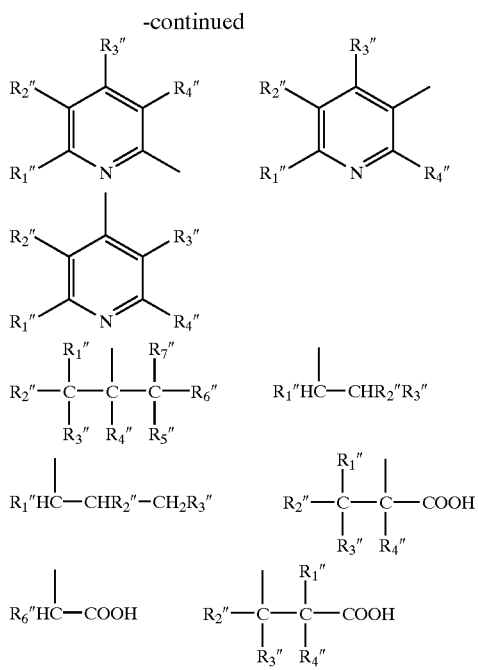

wherein R1", R2", R3", R4", R5", R6" and R7" independently of one another are a hydrogen atom, a methyl group, a halogen atom, a hydroxy group, a C1 to C4 hydroxyalkyl group, a benzyl group, an optionally substituted aromatic carbon ring or heterocyclic ring, a methoxy group, an ethoxy group, a carboxy group, an —NH$_2$ group, an —NHR$^b$ group, an —N(R$^b$)$_2$ group, in which R$^b$ is a hydrogen atom, a linear or branched C1 to C4 alkyl group, a C1 to C4 hydroxyalkyl group, an optionally substituted aromatic carbon ring or an optionally substituted aromatic heterocyclic ring and R8" is a group, required to form a natural α-amino acid (such as the (CH$_2$)$_3$-guanidinyl group for forming the α-amino acid arginine, the CH$_2$-imidazoyl group for forming the α-amino acid histidine or the CH$_2$-indolyl group for forming the α-amino acid tryptophan).

Preferred are compounds of Formula (I), in which the R1 and R3 groups together with the nitrogen atom and the carbon atom of the basic enamine structure form a cyclic compound, R3 preferably being linked to the aromatic R1 group at the carbon, which is in the ortho position to the enamine-substituted carbon.

Especially preferred are the following enamines of Formula (III) to (X), in which X is a carbon atom, substituted with two C1 to C4 alkyl groups, which may be the same or different and, in particular, are two methyl groups, a carbon atom, substituted with a C1 to C4 alkyl group and a hydroxyl group, a sulfur atom, an alkylated nitrogen atom, a not-alkylated nitrogen atom or an oxygen atom, and R2 is a linear or branched C1 to C8 alkyl group, a linear or branched C1 to C8 hydroxyalkyl group, or a C1 to C8 alkoxyalkyl group, in which there may be oxygen atoms between the carbon atoms of the alkyl chain, R4 is hydrogen, a linear C1 to C4 alkyl group or a branched C1 to C4 alkyl group, R5, R6, R7 and R8 independently of one another are hydrogen, a linear or branched C1 to C4 alkyl group, a linear or branched C1 to C4 hydroxyalkyl group, a hydroxy group, a methoxy group, an amino group, a monoalkylamino group, a dialkylamino group, a benzyl group or a halogen atom (F, Cl, Br, I) and A$^-$ is chloride, bromide, iodide, sulfate, hydrogen sulfate, toluenesulfonate, benzenesulfonate, monomethyl sulfate, hexafluorophosphate, hexafluoroantimonate, tetrafluoroborate, tetraphenylborate, formate, acetate or propionate, the chloride ion, the tetrafluoroborate ion, the acetate ion and the hydrogen sulfate ion being particularly preferred.

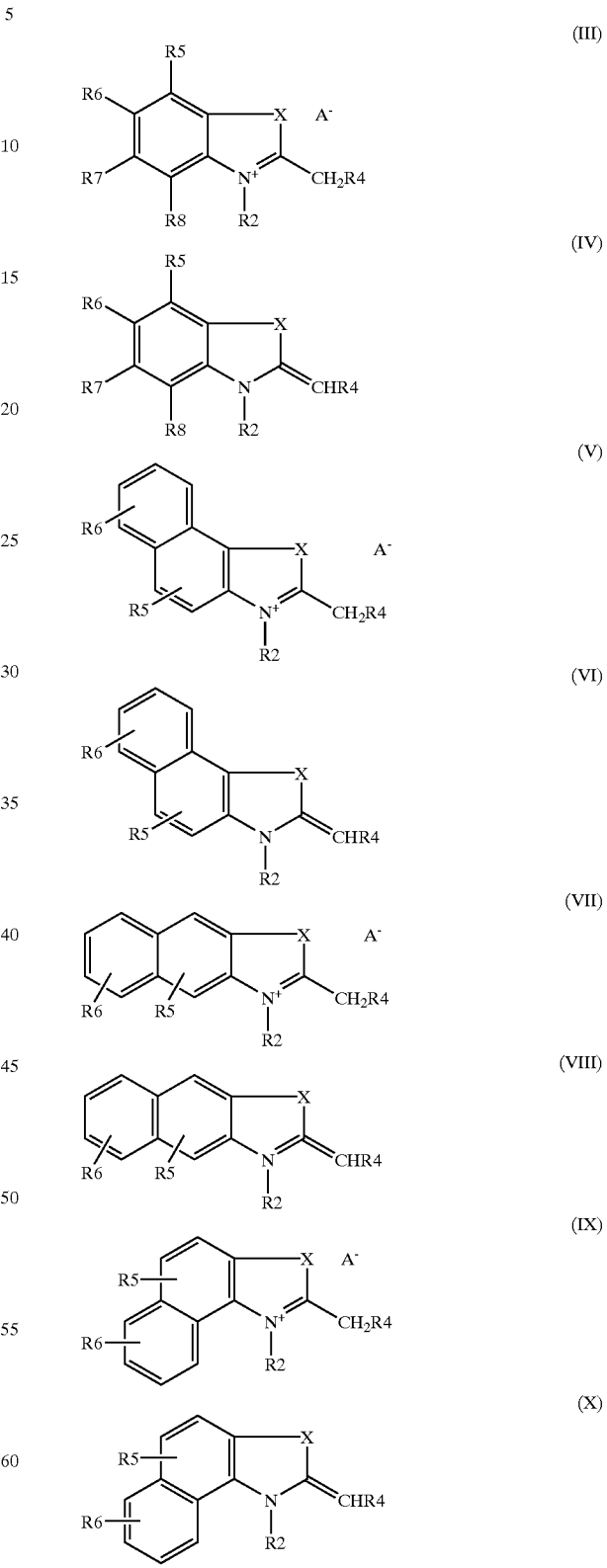

Of the compounds of the Formulas (III) to (X), especially the following should be mentioned: 1,3,3-trimethyl-2- methylene-indoline as well as its salts, 1,3,3,4-tetramethyl-2-methylene-indoline as well as its salts, 1,3,3,5-tetramethyl-2-methylene-indoline as well as its salts, 1,3,3,6-tetramethyl-2-methylene-indoline as well as its salts, 1,3,3,7-tetramethyl-2-methylene-indoline as well as its salts, 1,3,3,6,7-pentamethyl-2-methylene-indoline as well as its salts, 1,3,3,5,7-pentamethyl-2-methylene-indoline as well as its salts, 1,3,3,4,7-pentamethyl-2-methylene-indoline as well as its salts, 5-chloro-1,3,3-trimethyl-2-methylene-indoline as well as its salts, 5-fluoro-1,3,3-trimethyl-2-methylene-indoline as well as its salts, 5-isopropyl-1,3,3-trimethyl-2-methylene-indoline as well as its salts, 5-hydroxy-1,3,3-trimethyl-2-methylene-indoline as well as its salts, 5-methoxy-1,3,3-trimethyl-2-methylene-indoline as well as its salts, 5-amino-1,3,3-trimethyl-2-methylene-indoline as well as its salts, 5-N-acetylamino-1,3,3-trimethyl-2-methylene-indoline as well as its salts, 5-methoxy-6-N-acetylamino-1,3,3-trimethyl-2-methylene-indoline as well as its salts, 5-hydroxy-7-N-acetylamino-1,3,3-trimethyl-2-methylene-indoline as well as its salts, 6-hydroxy-1,3,3-trimethyl-2-methylene-indoline as well as its salts, 6-methoxy-1,3,3-trimethyl-2-methylene-indoline as well as its salts, 5-methoxy-6-amino-1,3,3-trimethyl-2-methylene-indoline as well as its salts, 5,6-dihydroxy-1,3,3-trimethyl-2-methylene-indoline as well as its salts, 5,6-dimethoxy-1,3,3-trimethyl-2-methylene-indoline as well as its salts, 4,5-dihydroxy-1,3,3-trimethyl-2-methylene-indoline as well as its salts, 5,7-dihydroxy-1,3,3-trimethyl-2-methylene-indoline as well as its salts, 5-amino-6-methoxy-1,3,3-trimethyl-2-methylene-indoline as well as its salts, 5-amino-7-hydroxy-1,3,3-trimethyl-2-methylene-indoline as well as its salts, 5-hydroxy-7-amino-1,3,3-trimethyl-2-methylene-indoline as well as its salts, 1-(2'-hydroxyethyl)-3,3-dimethyl-2-methylene-indoline as well as its salts, 1,3,3-trimethyl-2-methylene-3H-benz[e]indole as well as its salts and N-ethyl-2-methylene-benzthiazole as well as its salts, of which 1,3,3-trimethyl-2-methylene-indoline, 1,2,3,3-tetramethyl-3H-indolium chloride, 1,2,3,3-tetramethyl-3H-indolium bromide, 1,2,3,3-tetramethyl-3H-indolium iodide, 1,2,3,3-tetramethyl-3H-indoliumsulfate, 1,2,3,3-tetramethyl-3H-indolium-hydrogen sulfate, 1,2,3,3-tetramethyl-3H-indolium-methylsulfate, 1,2,3,3-tetramethyl-3H-indolium-hexafluorophosphate, 1,2,3,3-tetramethyl-3H-indolium-hexafluoroantimonate, 1,2,3,3-tetramethyl-3H-indolium-tetrafluoroborate, 1,2,3,3,5-pentamethyl-3H-indolium iodide, 1,2,3,3,7-pentamethyl-3H-indolium-tetrafluoroborate, 1,2,3,3,6,7-hexamethyl-3H-indolium-tetrafluoroborate, 1,2,3,3,5,7-hexamethyl-3H-indolium-tetrafluoroborate, 1,2,3,3,4,7-hexamethyl-3H-indolium-tetrafluoroborate, 5-chloro-1,2,3,3-tetramethyl-3H-indolium iodide, 5-fluoro-1,2,3,3-tetramethyl-3H-indolium iodide, 5-isopropyl-1,2,3,3-tetramethyl-3H-indolium iodide, 5-methoxy-1,2,3,3-tetramethyl-3H-indolium iodide, 5-hydroxy-1,2,3,3-tetramethyl-3H-indolium iodide, 1,2,3,3-tetramethyl-3H-benz[e]indolium chloride, 1,2,3,3-tetramethyl-3H-benz[e]indolium bromide, 1,2,3,3-tetramethyl-3H-benz[e]indolium iodide, 1,2,3,3-tetramethyl-3H-benz[e]indoliumsulfate, 1,2,3,3-tetramethyl-3H-benz[e]indolium-hexafluorophosphate, 1,2,3,3-tetramethyl-3H-benz[e]indolium-methylsulfate, 1,2,3,3-tetramethyl-3H-benz[e]indolium-hexafluoroantimonate, 1,2,3,3-tetramethyl-3H-benz[e]indolium-tetrafluoroborate, 1,2-dimethyl-benzothiazolium iodide and N-ethyl-2-methylbenzthiazolium iodide are especially preferred.

The Schiff's bases of Formula (II), used in the inventive preparation, can be synthesized by the reaction of the appropriate amines and carbonyl compounds by standard methods known from the literature, as described, for example, Houben-Weyl, "Methoden der organischen Chemie" (Methods of Organic Chemistry), Volume 7, Part 1, pages 453–460 (1954) or Jerry March "Advanced Organic Chemistry", $4^{th}$ Edition (1992), pages 896–898.

Of the compounds of Formula (II), the following are particularly preferred:
4-(((2-hydroxyethyl)imino)methyl)-2-methoxyphenol,
5-(((2-hydroxyethyl)imino)methyl)-2-methoxyphenol,
2,6-dimethoxy-4-(((2-hydroxyethyl)imino)methyl)phenol,
4-(((2-hydroxyethyl)imino)methyl) phenol,
1,2-dihydroxy-4-(((2-hydroxyethyl)imino)methyl)benzene,
N,N-dimethyl-4-(((2-hydroxyethyl)imino)methyl)-aniline,
1,2-dihydroxy-3-(((2-hydroxyethyl)imino)methyl)benzene,
4-(((3-hydroxypropyl)imino)methyl)phenol,
2,6-dimethoxy-4-(((3-hydroxypropyl)imino)methyl)phenol,
4-(((2,3-dihydroxypropyl)imino)methyl)phenol,
2,6-dimethoxy-4-(((2,3-dihydroxypropyl)imino)methyl) phenol,
2-[(4-hydroxy-benzylidene)-amino]-propane-1,3-diol,
2-[(4-hydroxy-3,5-dimethoxy-benzylidene)-amino]-propane-1,3-diol,
4-(((2-hydroxy-2-phenyl-ethyl)imino)methyl)phenol,
2,6-dimethoxy-4-(((1-phenyl-2-hydroxy-ethyl)imino) methyl)phenol,
4-(((2-hydroxyphenyl)imino)methyl)phenol,
2,6-dimethoxy-4-(((2-hydroxyphenyl)imino)methyl)phenol,
5-guanidino-2-[(4-hydroxy-benzylidene)-amino]-pentanoic acid,
2-[(4-dimethylamino-naphthalene-1-ylmethylene)-amino]-ethanol,
5-guanidino-2-[(4-hydroxy-3,5-dimethoxy-benzylidene)-amino]-pentanoic acid, 2-[(4-hydroxy-3,5-dimethoxy-benzylidene)-amino]-3-(3H-imidazole-4-yl)-propanoic acid, 2-[(4-hydroxy-benzylidene)-amino]-3-(3H-imidazole-4-yl)-propanoic acid, 2-[(4-hydroxy-3,5-dimethoxy-benzylidene)-amino]-3-(1H-indole-3-yl)-propanoic acid, 2-[(4-hydroxy-benzylidene)-amino]-3-(1H-indole-3-yl)-propanoic acid, 2-(((2-hydroxyethyl)imino)methyl)phenol, 1,2-dihydroxy-3-(((2-hydroxyethyl)imino)methyl)benzene, 1,2,3-trihydroxy-4-(((2-hydroxyethyl)imino)methyl)benzene, 1,2,3,4-tetrahydroxy-5-(((2-hydroxyethyl)-imino)methyl) benzene and 1,2,4-trihydroxy-4-(((2-hydroxyethyl) imino)-methyl)benzene.

The compounds of Formula (I) and the compounds of Formula (II) are kept separately from one another mixed only shortly before use.

The enamines of Formula (I), as well as the Schiff's bases of Formula (II), are contained in the ready-for-use component (A) in each case in a total amount of about 0.01 to 10% by weight and preferably 0.1 to 5% by weight.

Components (A1) and (A2) as well as the ready-for-use dyeing agent (A) may be in the form of a solution, particularly an aqueous or aqueous-alcoholic solution, a cream, a gel or an emulsion. Its composition represents a mixture of the enamines of Formula (I) and the Schiff's base of Formula (II) with the additives customary for such preparation.

Customary additives, used in dyeing agents in solutions, creams, emulsions, gels or aerosol foams are, for example, solvents such as water, low molecular weight aliphatic alcohols, such as ethanol, n-propanol and isopropanol, or glycols, such as glycerin and 1,2-dihydroxypropane, wetting agents or emulsifiers, from the classes of anionic, cationic, amphoteric or nonionic surface-active substances, such as fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty acid esters, thickeners, such as high molecular weight fatty alcohols, starch or cellulose derivatives, perfumes, hair pre-treatment materials, conditioners, hair-swelling agents, preservatives, Vaseline, paraffin oil and fatty acids, as well as care materials, such as cationic resins, lanolin derivatives, cholesterol, pantothenic acid and betaine. The components mentioned are used in amounts customary for such purposes; for example, the wetting agents and emulsifiers are used in concentrations of about 0.5 to 30% by weight, the thickeners in an amount of about 0.1 to 25% by weight and the care materials in a concentration of about 0.1 to 5.0% by weight.

Furthermore, the inventive dyeing agent optionally may contain additional, conventional, physiologically safe direct dyes from the group of nitro dyes, azo dyes, quinone dyes and triphenylmethane dyes. These direct dyes may be used in component (A1) and/or component (A2) in each case in a total amount of about 0.02 to 20% by weight and preferably of 0.2 to 10% by weight, the total amount of direct dyes in the ready-for-use dyeing agent, obtained by mixing components (A1) and (A2), being about 0.01 to 10% by weight and preferably 0.1 to 5% by weight.

The pH of the ready-for-use dyeing agent (A) usually is 3 to 12 and preferably about 6 to 11, the pH of the ready-for-use dyeing agent (A) during the mixing of the acidic component (A1) and the alkaline component (A2) reaching a value, which is affected by the amount of acid in component (A1) and the amount of alkali in component (A2), as well as by the ratio, in which these two components are mixed.

Component (A1) preferably has a pH of about 1 to 4.5 and especially of 1.5 to 3, while component (A2) preferably has a pH of 7.5 to 12 and especially 8 to 11.

For adjusting the pH of components (A1) and (A2) and of the ready-for-use dyeing agent (A) to the value desired for the coloring, alkalizing agents, such as alkanolamines, alkylamines, alkali hydroxides or ammonium hydroxide and alkali carbonates or ammonium carbonates, or acids, such as lactic acid, acetic acid, tartaric acid, phosphoric acid, hydrochloric acid, citric acid, ascorbic acid or boric acid may, if necessary, be used.

The ready-for-use dyeing agent is prepared immediately before use by mixing components (A1) and (A2) and then applied on the fibers, especially on human hair. This mixture is allowed to act for 5 to 60 minutes and preferably for 15 to 30 minutes at a temperature of about 20° C. to 50° C. and especially at 30° C. to 40° C., depending on the depth of color desired. Subsequently, the fibers are rinsed with water and optionally washed with a shampoo.

A further object of the present invention is a multi-component kit, consisting of a preparation of component (A1), a preparation of component (A2), as well as, optionally, a preparation for adjusting the pH. Of course, the preparations of components (A1) and (A2) may also consist of several individual components, which are mixed together only immediately before use. However, a two-component kit, consisting of a preparation of component (A1) and a preparation of component (A2), is particularly preferred.

The inventive dyeing agent has a long shelf life and enables the fibers, especially keratin fibers such as human hair, to be colored gently, uniformly and durably, the coloration obtained not becoming darker afterwards. Surprisingly, these colorations can be removed again in a simple and gentle manner at any time by sulfites.

A further object of the present invention therefore is a method for temporarily coloring fibers, for which the fibers initially are colored with the inventive dyeing agent (A) and the coloration is removed once again at any later time with a decolorizing agent, which contains at least one sulfite, as well as a multi-component kit for dyeing and later decolorizing fibers, containing the inventive dyeing agent (A) as well as a sulfite-containing decolorizing agent (B).

As sulfite, ammonium sulfite, alkali sulfites or alkaline earth sulfites, for example, can be used, sodium sulfite and ammonium sulfite being particularly preferred. The total amount of sulfite in the decolorizing agent is about 0.1 to 10% by weight and preferably 2 to 5% by weight.

This decolorizing agent can be in the form of an aqueous or an aqueous alcoholic solution, a gel, a cream, an emulsion or a suspension. Moreover, the decolorizing agent can be in the form of a one-component preparation as well as in the form of a multi-component preparation. Aside from being in powder form, the decolorizing agent may also be in the form of a tablet, such as an effervescent tablet, or a granulate, as protection against the formation of dust. Before use, the decolorizing agent is prepared from this with cold or warm water, optionally with the addition of one or more of the adjuvants named below. It is, however, also possible that these adjuvants, if they are in solid form, are already contained in the decolorizing powder or decolorizing granulates or the effervescent tablet. Dust formation can be reduced additionally by wetting the powder with oils or waxes.

The dyeing agent may contain additional adjuvants, for example, solvents such as water, low molecular weight alcohols, such as ethanol, n-propanol and isopropanol, glycol ethers or glycols, such as glycerin and, in particular 1,2-dihydroxy propane, wetting agents or emulsifiers from the classes of anionic, cationic, amphoteric or nonionic surface-active substances, such as fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides, ethoxylated fatty alcohols, ethoxylated nonylphenol, fatty acid alkanolamides, ethoxylated fatty acid esters, thickeners such as high molecular weight fatty alcohols, starch or cellulose derivates, perfumes, hair-pre-treatment preparations, conditioners, hair swelling agents, preservatives, Vaseline, paraffin oil and fatty acids, as well as care materials, such as cationic resins, lanolin derivatives, cholesterol, pantothenic acid and betaine.

The pH of the decolorizing agent is about 3 to 8 and especially 4 to 7. If necessary, the desired pH can be obtained by adding suitable acids, for example, α-hydroxycarboxylic acids, such as lactic acid, tartaric acid, citric acid or maleic acid, phosphoric acid, acetic acid, glycolic acid, salicylic acid, glutathione or gluconic acid lactone, or alkalizing agents such as alkanolamines, alkylamines, alkali hydroxides, ammonium hydroxide, alkali carbonates, ammonium carbonates or alkali phosphates.

For decolorizing fibers colored with the inventive preparation, the decolorizing agent is applied on the fibers and allowed to act at about 20° C. to 50° C. for a period of 5 to 60 minutes and especially 15 to 30 minutes. At the end of the period of action of the decolorizing agent, the hair is rinsed with water, optionally washed with a shampoo and subsequently dried.

The following examples are intended to explain the object in greater detail without limiting it to the examples.

EXAMPLES

Examples 1.1 to 1.19

Synthesis of the Schiff's Bases of Formula (II)
General Synthesis Method
Method A:

The carbonyl compound is dissolved in toluene at 80 C. and mixed with 1 equivalent of the primary amine. The mixture is refluxed with a water separator. When water of reaction is no longer formed, the solvent is distilled off under reduced pressure. The residue formed is purified by recrystallization.
Method B:

The carbonyl compound is dissolved at room temperature in chloroform, mixed with 1 equivalent of the primary amine and stirred for about 1 hour at room temperature. If the Schiff's base precipitates, the solid formed is filtered off; otherwise, the solvent is distilled off under reduced pressure. The filter solid or the residue obtained is purified by recrystallization.
Method C:

The carbonyl compound is dissolved in t-butyl methyl ether at 20° C. to 55° C., mixed with 1 equivalent of the primary amine and stirred for 1 to 3 hours at room temperature or heated for 1 to 3 hours under reflux. The solvent is removed under reduced pressure and the solid formed is purified by recrystallization.

Example 1.1

Synthesis of 4-(((2-hydroxyethyl)imino)methyl)-2-methoxyphenol

The synthesis is carried out according to method A, 6.25 g of 4-hydroxy-3-methoxybenzaldehyde and 2.50 mL of monoethanolamine being reacted in 250 mL of toluene. The resulting residue is recrystallized from ethyl acetate.

Yield: 6.41 g (80% of the theoretical) of 4-(((2-hydroxyethyl)imino)methyl-2-methoxyphenol Melting point: 129° C.

$^1$H-NMR (D$_6$-DMSO): δ=3.52–3.58 ppm (m, 2H); 3.58–3.64 ppm (m, 2H), 3.78 ppm (s, 3H); 6.79 ppm (d, $^3$J=8 Hz, 1H); 7.08 ppm (dd, $^3$J=8.0 Hz, $^4$J=2.0 Hz, 1H); 7.32 ppm (d, $^3$J-2.0 Hz, 1H); 8.14 ppm (s, 1H).

$^{13}$C-NMR (D$_6$-DMSO): δ=55.5 ppm (q); 61.0 ppm (t); 63.1 ppm (t); 109.9 ppm (d); 115.2 ppm (d); 122.8 ppm (d); 127.8 ppm (s); 147.9 ppm (s); 149.5 ppm (s); 161.3 ppm (d).

E1 mass spectrum: 195 (26, M$^+$); 164 (71); 150 (7); 137 (100); 122 (16); 104 (41); 94 (18); 77 (18); 65 (26); 51 (21).

| Elementary analysis: C$_{10}$H$_{13}$NO$_3$ (195.22) | | | |
|---|---|---|---|
| | % C | % H | % N |
| calc. | 61.53 | 6.71 | 7.17 |
| found | 61.0 | 6.77 | 7.06 |

Example 1.2

Synthesis of 5-(((2-hydroxyethyl)imino)methyl)-2-methoxyphenol

The synthesis is carried out according to Method A, 5.0 g 3-hydroxy-4-methoxybenzaldehyde and 2.0 mL of monoethanolamine being reacted in 150 mL of toluene. The resulting residue is recrystallized from chloroform.

Yield: 5.61 g (87% of the theoretical) of 5(((2-hydroxyethyl)imino)methyl)-2-methoxyphenol Melting-point: 114° C.–116° C.

$^1$H-NMR (MeOD): δ=3.70 ppm (t, $^3$J=5.5 Hz, 2H); 3.84 ppm (t, $^3$J=5.5 Hz, 2H); 3.93 ppm (s, 3H); 7.00 ppm (d $^3$J=8.5 Hz, 1H); 7.21 ppm (dd, $^3$J=8.5 Hz, $^4$J=2.0 Hz, 1H); 7.31 ppm (d, $^4$J=2.0 Hz, 1H); 8.22 ppm (s, 1H).

$^{13}$C-NMR (MeOD): δ=56.4 ppm (q); 62.4 ppm (t); 64.0 ppm (t); 112.1 ppm (d); 114.9 ppm (d); 122.9 ppm (d); 130.3 ppm (s); 147.9 ppm (s); 151.9 ppm (s); 165.5 ppm (d).

FAB-mass spectrum: M$^+$=169.2 (100% relative intensity)

| Elementary analysis: C$_{10}$H$_{13}$NO$_3$ (195.22) | | | |
|---|---|---|---|
| | % C | % H | % N |
| calc. | 61.53 | 6.71 | 7.18 |
| found | 61.76 | 6.94 | 7.06 |

Example 1.3

Synthesis of 2,6-dimethoxy-4-(((2-hydroxyethyl)imino)methyl)phenol

The synthesis is carried out according to Method B, 5.0 g of 3,5-dimethoxy-4-hydroxybenzaldehyde and 1.70 mL of monoethanolamine being reacted in 50 mL of chloroform. The resulting residue is recrystallized from acetonitrile.

Yield: 6.19 g (84% of the theoretical) of 2,6-dimethoxy-4-(((2-hydroxyethyl)imino)methyl)phenol $^1$H-NMR (MeOD): δ=3.71 ppm (t, $^3$J=5.5 Hz, 2H); 3.85 ppm (t, $^3$J=5.5 Hz, 2H); 3.89 ppm (s, 6H); 7.11 ppm (s, 2H); 8.16 ppm (s, 1H).

$^{13}$C-NMR (D$_6$-DMSO): δ=56.1 ppm (q); 61.1 ppm (t); 63.1 ppm (t); 105.6 ppm (d); 126.5 ppm (s); 138.9 ppm (s); 148.2 ppm (s); 161.6 ppm (d).
Electrode E1 mass spectrum: 225 (14, M$^+$); 194 (48); 180 (9); 179 (10); 167 (14); 162 (48); 148 (28); 134 (100); 107 (50); 79 (32); 65 (18).

| Elementary analysis: C$_{11}$H$_{15}$NO$_4$ x 1 CH$_3$CN (266.30) | | | |
|---|---|---|---|
| | % C | % H | % N |
| calc. | 58.63 | 6.81 | 10.52 |
| found | 57.85 | 6.91 | 9.49 |

Example 1.4

Synthesis of 4-(((2-hydroxyethyl)imino)methyl)phenol

The synthesis is carried out according to Method C, 2.0 g of 4-hydroxybenzaldehyde and 1.0 mL of monoethanolamine being reacted in 30 mL of t-butyl methyl ether. The resulting residue is recrystallized from 1-butanol.

Yield: 2.20 g (83% of the theoretical) of 4-(((2-hydroxyethyl)imino)methyl)phenol $^1$H-NMR (MeOD): δ=3.69 ppm (t, $^3$J=5.5 Hz, 2H); 3.83 ppm (t, $^3$J=5.5 Hz, 2H); 6.84 ppm (~d, $^3$J~8.5 Hz, 2H); 7.64 ppm (~d, $^3$J~8.5 Hz, 2H); 8.23 ppm (s, 1H).

$^{13}$C-NMR (MeOD): δ=62.3 ppm (t); 63.3 ppm (t); 117.0 ppm (d); 127.4 ppm (s); 131.7 ppm (d); 163.4 ppm (s); 165.5 ppm (d).

EI mass spectrum: 165 (31, M$^+$); 134 (99); 120 (22); 107 (100); 93 (8); 77 (62); 65 (22); 51 (12).

| Elementary analysis: C$_9$H$_{11}$NO$_2$ (165.19) | | | |
|---|---|---|---|
| | % C | % H | % N |
| calc. | 65.44 | 6.71 | 8.48 |
| found | 65.74 | 6.94 | 8.36 |

Example 1.5

Synthesis of 1,2-dihydroxy-4-(((2-hydroxyethyl)imino)methyl)benzene

The synthesis is carried out according to Method C, 5.0 g of 3,4-dihydroxybenzaldehyde and 2.20 mL of monoethanolamine being reacted in 100 mL of t-butyl methyl ether. The resulting residue is dissolved in hot isopropanol and allowed to cool and the solid formed is discarded. The filtrate is subsequently evaporated under reduced pressure and the residue is recrystallized from 1-butanol.

Yield: 2.70 g (41% of the theoretical) of 1,2-dihydroxy-4-(((2-hydroxyethyl)imino)-methyl)benzene Melting point: 103° C.–107° C.

$^1$H-NMR (MeOD): δ=3.67 ppm (t, $^3$J=5.5 Hz, 2H); 3.82 ppm (t, $^3$J=5.5 Hz, 2H); 6.77 ppm (d, $^3$J=8 Hz, 1H); 7.14 ppm (d, $^3$J=8 Hz, 1H); 7.26 ppm (s, 1H); 8.09 ppm (s, 1H).

$^{13}$C-NMR (MeOD): δ=61.4 ppm (t); 62.2 ppm (t); 113.8 ppm (d); 116.8 ppm (d); 124.8 ppm (s); 126.5 ppm (d); 147.9 ppm (s); 156.1 ppm (s); 165.5 (d).

Example 1.6

Synthesis of N,N-dimethyl-4-(((2'-hydroxyethyl)imino)-methyl)aniline

The synthesis is carried out according to Method C, 5.0 g of 4-(dimethylamino)benzaldehyde and 2.0 mL of monoethanolamine being reacted in 50 mL of t-butyl methyl ether. The resulting residue is recrystallized from acetonitrile.

Yield: 5.21 g (81% of the theoretical) of N,N-dimethyl-4-(((2'-hydroxyethyl)imino)methyl)aniline Melting point: 103° C.–105° C.

$^1$H-NMR (MeOD): δ=3.03 ppm (s, 6H); 3.67 ppm (t, $^3$J=5.5 Hz, 2H); 3.82 ppm (t, $^3$J=5.5 Hz, 2H); 6.77 ppm (~d, ~$^3$J=9 Hz, 2H); 7.62 ppm (~d, ~$^3$J=9 Hz, 1H); 8.19 ppm (s, 1H).

EI mass spectrum: 192 (85, M$^+$); 161 (100); 146 (70); 134 (88); 117 (56); 91 (30); 81 (25);

| Elementary analysis: C$_{11}$H$_{16}$NO$_2$ (192.26) | | | |
|---|---|---|---|
| | % C | % H | % N |
| calc. | 68.72 | 8.39 | 14.57 |
| found | 68.90 | 8.60 | 14.58 |

Example 1.7

Synthesis of 1,2-dihydroxy-3-(((2-hydroxyethyl)imino)-methyl)benzene

The synthesis is carried out according to Method C, 2.0 g of 2,3-dihydroxybenzaldehyde and 0.9 mL of monoethanolamine being reacted in 30 mL of t-butyl methyl ether. The resulting residue is recrystallized from ethylacetate.

Yield: 2.08 g (79% of the theoretical) of 1,2-dihydroxy-3-(((2-hydroxyethyl)imino)methyl)benzene Melting point: 112° C.–116° C.

$^1$H-NMR (MeOD): δ=3.75 ppm (t, $^3$J=5.0 Hz, 2H); 3.84 ppm (t, $^3$J=5.0 Hz, 2H); 6.60–6.66 ppm (m, 1H); 6.84–6.90 ppm (m, 2H); 8.40 ppm (s, 1H).

| Elementary analysis: C$_9$H$_{11}$NO$_3$ (181.19) | | | |
|---|---|---|---|
| | % C | % H | % N |
| calc. | 59.66 | 6.12 | 7.73 |
| found | 59.63 | 6.19 | 7.60 |

Example 1.8

Synthesis of 4-(((3-hydroxypropyl)imino)methyl)phenol

The synthesis is carried out according to Method C, 5.0 g of 4-hydroxybenzaldehyde and 3.08 mL of 3-amino-1-propanol being reacted in 70 mL of t-butyl methyl ether. The resulting residue is recrystallized from acetonitrile.

Yield: 5.62 g (77% of the theoretical) of 4-(((3-hydroxypropyl)imino)methyl)-phenol Melting point: 110° C.–115° C.

$^1$H-NMR (MeOD): δ=1.88–1.97 ppm (m, 2H); 3.65–3.70 ppm (m, 4H); 6.84 ppm (~d, ~$^3$J=9 Hz, 2H); 7.62 ppm (~d, ~$^3$J=9 Hz, 2H); 8.23 ppm (s, 1H).

| Elementary analysis: C$_{10}$H$_{13}$NO$_2$ (179.22) | | | |
|---|---|---|---|
| | % C | % H | % N |
| calc. | 67.02 | 7.31 | 7.82 |
| found | 67.30 | 7.59 | 7.82 |

Example 1.9

Synthesis of 2,6-dimethoxy-4-(((3-hydroxypropyl)imino)methyl)phenol

The synthesis is carried out according to Method C, 5.0 g of 3,5-dimethoxy-4-hydroxybenzaldehyde and 2.06 g of 3-amino-1-propanol being reacted in 100 mL of t-butyl methyl ether. The resulting residue is recrystallized from acetonitrile.

Yield: 2.20 g (33% of the theoretical) of 2,6-dimethoxy-4-(((3-hydroxypropyl)imino)-methyl)phenol Melting point: 143° C.–146° C.

$^1$H-NMR (MeOD): δ=1.90–2.00 ppm (m, 2H); 3.66–3.72 ppm (m, 4H); 3.89 ppm (s, 6H); 7.09 ppm (s, 2H); 8.16 ppm (s, 1H).

E1 mass spectrum: 239 (26, M$^+$); 209 (30); 194 (100); 180 (52); 164 (32); 134 (44); 120 (20); 107 (28); 94 (20); 79 (26).

| Elementary analysis: $C_{12}H_{17}NO_4$ (239.27) | | | |
|---|---|---|---|
| | % C | % H | % N |
| calc. | 60.24 | 7.16 | 5.85 |
| found | 59.99 | 7.44 | 5.77 |

Example 1.10

Synthesis of 4-(((2,3-dihydroxypropyl)imino)methyl)phenol

The synthesis is carried out according to Method C, 5.0 g of 4-hydroxybenzaldehyde and 3.73 g of 3-amino-1,2-dihydroxypropane being reacted in 70 mL of t-butyl methyl ether. The resulting residue is recrystallized from toluene.

Yield: 6.75 g (84% of the theoretical) of 4-(((2,3-dihydroxypropyl)imino)methyl)phenol Melting point: 125° C.–131° C.

$^1$H-NMR (MeOD): δ=3.45–3.55 ppm (m, 1H); 3.55–3.70 ppm (m, 2H); 3.75–3.85 ppm (m, 1H); 3.85–4.0 ppm (m, 1H); 6.84 ppm (~d, ~$^3$J=9 Hz, 2H); 7.64 ppm (~d, ~$^3$J=9 Hz, 2H); 8.23 ppm (s, 1H).

| Elementary analysis: $C_{10}H_{13}NO_3$ (195.22) | | | |
|---|---|---|---|
| | % C | % H | % N |
| calc. | 61.53 | 6.71 | 7.18 |
| found | 61.62 | 6.89 | 7.10 |

Example 1.11

Synthesis of 2,6-dimethoxy-4-(((2,3-dihydroxypropyl)imino)methyl)phenol

The synthesis is carried out according to Method B, 5.0 g of 3,5-dimethoxy-4-hydroxybenzaldehyde and 2.50 g of 3-amino-1,2-dihydroxypropane being reacted in 50 mL of chloroform. The resulting residue is recrystallized from isopropanol.

Yield: 3.12 g (45% of the theoretical) of 2,6-dimethoxy-4-(((2,3-dihydroxypropyl)imino)methyl)phenol Melting point: 124° C.–128° C.

$^1$H-NMR (MeOD): δ=3.48–3.60 ppm (m, 1H); 3.60–3.70 ppm (m, 2H); 3.75–4.0 ppm (m, 2H); 3.90 ppm (s, 6H); 7.12 ppm (s, 2H); 8.17 ppm (s, 1H).

| Elementary analysis: $C_{12}H_{17}NO_5$ (255.27) | | | |
|---|---|---|---|
| | % C | % H | % N |
| calc. | 55.46 | 6.71 | 5.49 |
| found | 56.49 | 6.83 | 5.35 |

Example 1.12

Synthesis of 2-[(4-hydroxy-benzylidene)-amino]-propane-1,3-diol

The synthesis is carried out according to Method A, 2.44 g of 4-hydroxybenzaldehyde and 1.82 g of 2-amino-1,3-dihydroxypropane being reacted in 80 mL of toluene. The resulting residue is recrystallized from methanol.

Yield: 0.48 g (12% of the theoretical) of 2-[(4-hydroxy-benzylidene)-amino]-propane-1,3-diol $^1$H-NMR (MeOD/D$_6$-DMSO): δ=3.40–3.60 ppm (m, 1H); 3.65–3.80 ppm (m, 2H); 3.80–3.95 ppm (m, 2H); 6.93 ppm (m, 2H); 7.75 ppm (m, 2H); 8.35 ppm (s, 1H).

| Elementary analysis: $C_{10}H_{13}NO_3$(195.22) | | | |
|---|---|---|---|
| | % C | % H | % N |
| calc. | 61.53 | 6.71 | 7.18 |
| found | 61.48 | 6.92 | 6.90 |

Example 1.13

Synthesis of 2-[(4-hydroxy-3,5-dimethoxy-benzylidene)-amino]-propane-1,3-diol

The synthesis is carried out according to Method A, 2.0 g of 3,5-dimethoxy-4-hydroxybenzaldehyde and 1.0 g of 2-amino-1,3-dihydroxypropane being reacted in 80 mL of toluene. The resulting residue is recrystallized from acetonitrile.

Yield: 2.10 g (75% of the theoretical) of 2-[(4-hydroxy-3,5-dimethoxy-benzylidene)-amino]-propane-1,3-diol Melting point: 196° C.–199° C.

$^1$H-NMR (MeOD): δ=3.40–3.60 ppm (m, 1H); 3.60–3.75 ppm (m, 2H); 3.75–3.90 ppm (m, 2H); 3.92 ppm (s, 6H); 7.17 ppm (s, 2H); 8.24 ppm (s, 1H).

ES-Mass spectrum: (M$^+$–1)=254.1 (100% relative intensity)

Example 1.14

Synthesis of 4-(((2-hydroxy-2-phenyl-ethyl)imino)methyl)phenol

The synthesis is carried out according to Method A, 4.27 g of 4-hydroxybenzaldehyde and 4.08 g of 2-amino-1-phenylethanol being reacted in 100 mL of toluene. The resulting residue is recrystallized from toluene.

Yield: 7.95 g (94% of the theoretical) of 4-(((2-hydroxy-2-phenyl-ethyl)imino)methyl)phenol Melting point: 165° C.–169° C.

$^1$H-NMR (MeOD): δ=3.65–3.80 ppm (m, 1H); 3.80–3.95 ppm (m, 1H); 4.95–5.05 ppm (m, 1H); 6.83 ppm (~d, ~$^3$J=9

Hz, 2H); 7.22–7.50 ppm (m, 5H); 7.62 ppm (~d, ~$^3$J=9 Hz, 2H); 8.13 ppm (s, 1H).

ES-Mass spectrum: (M$^+$−1)=240.1 (100% relative intensity)

| Elementary analysis: C$_{15}$H$_{15}$NO$_2$(241.29) | | | |
|---|---|---|---|
| | % C | % H | % N |
| calc. | 74.67 | 6.27 | 5.81 |
| found | 74.73 | 6.42 | 5.56 |

Example 1.15

Synthesis of 2,6-dimethoxy-4-(((1-phenyl-2-hydroxy-ethyl)imino)methyl)phenol

The synthesis is carried out according to Method A, 2.66 g of 3,5-dimethoxy-4-hydroxybenzaldehyde and 2.0 (R)-2-amino-1-phenylethanol being reacted in 80 mL of toluene. The resulting residue is recrystallized from a 1:3 mixture of toluene and petroleum ether.

Yield: 4.05 g (92% of the theoretical) of 2,6-dimethoxy-4-(((1-phenyl-2-hydroxy-ethyl)imino)methyl)phenol Melting point: 58° C.–62° C.

$^1$H-NMR (MeOD): δ=3.85–4.0 ppm (m, 2H); 3.90 ppm (s, 6H); 4.48 ppm (m, 1H); 7.10–7.50 ppm (m, 7H); 8.32 ppm (s, 1H).

ES-Mass spectrum: (M$^+$−1)=300.10 (100% relative intensity)

| Elementary analysis: C$_{17}$H$_{19}$NO$_4$(301.35) | | | |
|---|---|---|---|
| | % C | % H | % N |
| calc. | 67.76 | 6.36 | 4.65 |
| found | 67.48 | 6.57 | 4.15 |

Example 1.16

Synthesis of 4-(((2-hydroxyphenyl)imino)methyl)phenol

The synthesis is carried out according to Method A, 5.0 g of 4-hydroxybenzaldehyde and 4.47 g of 2-aminophenol being reacted in 100 mL of toluene. The resulting residue is recrystallized from toluene.

Yield: 8.51 g (97% of the theoretical) of 4-(((2-hydroxyphenyl)imino)methyl)phenol Melting point: 145° C.–149° C.

$^1$H-NMR (MeOD): δ=6.80–7.00 ppm (m, 4H); 7.05–7.25 ppm (m, 2H); 7.80–7.90 ppm (m, 2H); 8.56 ppm (s, 1H).

EL Mass spectrum: 213 (76, M$^+$); 212 (92); 120 (100); 107 (12); 93 (30); 77 (22); 65 (64); 51 (24).

| Elementary analysis: C$_{13}$H$_{11}$NO$_2$(213.24) | | | |
|---|---|---|---|
| | % C | % H | % N |
| calc. | 73.23 | 5.20 | 6.57 |
| found | 72.98 | 5.29 | 6.25 |

Example 1.17

Synthesis of 2,6-dimethoxy-4-(((2-hydroxyphenyl)imino)methyl)phenol

The synthesis is carried out according to Method A, 4.92 g of 3,5-dimethoxy-4-hydroxybenzaldehyde and 2.95 g of 2-aminophenol being reacted in 100 mL of toluene. The resulting residue is recrystallized from toluene.

Yield: 6.24 g (83% of the theoretical) of 2,6-dimethoxy-4-(((2-hydroxyphenyl)imino)methyl)phenol $^1$H-NMR (MeOD): δ=3.94 ppm (s, 6H); 6.83–6.98 ppm (m, 2H); 7.05–7.22 ppm (m, 2H); 7.33 ppm (s, 2H); 8.52 ppm (s, 1H).

EL Mass spectrum: 273 (75, M$^+$); 256 (10); 170 (10); 154 (52); 139 (26); 120 (100); 93 (30); 77 (18); 65 (44).

| Elementary analysis: C$_{15}$H$_{15}$NO$_4$(273.29) | | | |
|---|---|---|---|
| | % C | % H | % N |
| calc. | 65.93 | 5.53 | 5.13 |
| found | 66.11 | 5.62 | 5.00 |

Example 1.18

Synthesis of 5-guanidino-2-[(4-hydroxy-benzylidene)-amino]-pentanoic Acid

The synthesis is carried out according to Method A, 3.0 g of 4-hydroxybenzaldehyde and 4.28 g of L-arginine being reacted in 100 mL of toluene. The resulting residue is recrystallized from methanol.

Yield: 2.29 g (25% of the theoretical) of 5-guanidino-2-[(4-hydroxy-benzylidene)-amino]-pentanoic acid $^1$H-NMR (MeOD): δ=1.58–1.75 ppm (mn, 2H); 1.83–2.10 ppm (m, 2H); 3.15–3.28 ppm (m, 2H); 3.87 ppm (m, 1H); 6.81 ppm (~d, ~$^3$J=9 Hz, 2H); 7.67 ppm (~d, ~$^3$J=9 Hz, 2H); 8.19 ppm (s, 1H).

FAB-Mass spectrum: 279.0 (M$^+$, 30% relative intensity)

Example 1.19

Synthesis of 2-[(4-dimethylamino-naphthalene-1-ylmethylene)-amino]-ethanol

The synthesis is carried out according to Method B, 3.0 g of 4-(dimethylamino)-naphthalene-1-carboxyaldehyde and 0.92 g of monoethanolamine being reacted in 20 mL of chloroform. After being stirred for about 7 hours at room temperature, the reaction solution is evaporated completely. According to analytical data, the resulting residue, an oil, is a pure product.

Yield: 3.60 g (99% of the theoretical) of 2-[(4-dimethylamino-naphthalene-1-ylmethylene)-amino]-ethanol $^1$H-NMR (DMSO): δ=2.86 ppm (s, 6H); 3.71 ppm (m, 4H); 4.62 ppm (s, br, 1H); 7.11 ppm (d, $^3$J=8 Hz, 1H); 7.50–7.60 ppm (m, 2H); 7.78 ppm (d, $^3$J=8 Hz, 1H); 8.16 ppm (~d, ~$^3$J=9 Hz, 1H) 8.78 ppm (s, 1H); 9.19 ppm (~d, ~$^3$J=9 Hz, 1H).

E1 Mass spectrum: 242 (100, M$^+$); 227 (10); 211 (50); 196 (40); 167 (22); 154 (10); 139 (12); 127 (8); 115 (8).

Elementary analysis:
—C$_{15}$H$_{18}$N$_2$O × 0.7 H$_2$O (254.93)

|  | % C | % H | % N |
|---|---|---|---|
| calc. | 70.67 | 7.67 | 10.99 |
| found | 70.58 | 7.54 | 11.04 |

Examples 2.1 to 2.20

Hair Coloring Preparation

Component (A1)

| Enamine of Formula (I) | Quantitative data in Table 1 |
|---|---|
| 6-O-palmitoyl-L-ascorbic acid | 0.3 g |
| cetyl stearyl alcohol | 12.0 g |
| lauryl ether sulfate, 28% aqueous solution | 100.0 g |
| ethanol | 23.0 g |
| water, fully desalinated | ad 100.0 g |

The cetyl stearyl alcohol is melted at 80° C. The lauryl ether sulfate and 95% of the water are heated to 80° C. and added to the molten cetyl stearyl alcohol and stirred until a cream results. The compound of Formula (I), the ethanol, the remaining water and the 6-O-palmitoyl-L-ascorbic acid are added at room temperature. The pH of the material is given in Table 1.

Component (A2)

| Shiff's Base of Formula (II) | Quantitative data in Table 1 |
|---|---|
| cetyl stearyl alcohol | 12.0 g |
| lauryl ether sulfate, 28% aqueous solution | 10.0 g |
| ethanol | 23.0 g |
| water, fully desalinated | ad 100.0 g |

The cetyl stearyl alcohol is melted at 80° C. The lauryl ether sulfate and 95% of the water are heated to 80° C. and added to the molten cetyl stearyl alcohol and stirred until a cream results. The compound of formula (I), together with ethanol and the remaining water, is added at room temperature. The pH of the cream is adjusted with a suitable primary amine or with 10% sodium hydroxide to the value given in Table 1.

Component (A1) and Component (A2) are mixed in a ratio of 1:1. The ready-for-use hair coloring preparation, so obtained, is applied on the hair and distributed uniformly with a brush. After a period of action of 30 minutes at 40° C., the hair is washed with a shampoo, subsequently rinsed with lukewarm water and then dried.

The hair can be decolorized once again completely at any time, for example, after several days or weeks, with a 5% sodium sulfite solution (pH=5) within a period of 20 minutes at 40° C. The coloring and decolorizing results are given in the following Table 1.

The L*a*b* measured color values are determined with a Minolta Chromameter II calorimeter. The L value represents the luminosity (this means that L value varies inversely with the color intensity), while the a value is a measure of the red portion (that is, the a value varies with the red portion) and the b value is a measure of the blue portion of the color, a more negative b value indicating a greater proportion of blue.

Unless stated otherwise, all percentages in the present applications are percentages by weight.

TABLE 1

Color Results

| No. | Enamine of Formula (I), contained in Component (A1) Schiff's Base of Formula (II), contained in Component (A2) | Shade after the coloring | | Measured Color Values | | | Shade after decolorizing |
|---|---|---|---|---|---|---|---|
| | | | | L | a | b | |
| 2.1 | (A1) 1,2,3,3-tetramethyl-3H-indolium-hydrogen sulfate: 3.12 g, pH = 1.7; (A2) 4-(((2-hydroxyethyl)imino)-methyl)-2-methoxyphenol: 2.24 g and monoethanolamine to pH = 9.5 | intensive red | Untreated hair: After the coloring: | +83.30; +32.50 | −0.48; +54.44; | +10.40 +17.61 | white |
| 2.2 | (A1) 1,2,3,3-tetramethyl-3H-indolium chloride: 2.42 g, pH = 1.7; (A2) 5-(((2-hydroxyethyl)imino)-methyl)-2-methoxyphenol: 2.24 g and monoethanolamine to pH 9.6 | intensive yellow | Untreated hair: After the coloring: | +83.30; +67.73 | −0.48; +24.42; | +10.40 +83.08 | white |

TABLE 1-continued

Color Results

| No. | Enamine of Formula (I), contained in Component (A1) Schiff's Base of Formula (II), contained in Component (A2) | Shade after the coloring | | Measured Color Values | | | Shade after decolorizing |
| --- | --- | --- | --- | --- | --- | --- | --- |
| | | | | L | a | b | |
| 2.3 | (A1) 1,2,3,3-tetramethyl-3H-indolium chloride: 2.42 g, pH = 1.7; (A2) 2,6-dimethoxy-4-(((2-hydroxyethyl)imino)methyl)phenol: 2.59 g and monoethanolamine to pH = 9.6 | intensive violet | Untreated hair: After the coloring: | +83.30; +23.96 | −0.48; +43.17; | +10.40 −2.65 | white |
| 2.4 | (A1) 1,2,3,3-tetramethyl-3H-indolium hydrogen sulfate: 3.13 g, pH = 1.7; (A2) 4-(((2-hydroxyethyl)imino).-methyl)phenol: 1.90 g and monoethanolamine to pH 9.4 | intensive oramge | Untreated hair: After the coloring: | +83.30; +49.31 | −0.48; +61.17; | +10.40 +55.04 | white |
| 2.5 | (A1) 1,2,3,3-tetramethyl-3H-indolium hydrogen sulfate: 3.13 g, pH = 1.7; (A2) 1,2-dihydroxy-4-(((2-hydroxyethyl)imino)methyl)benzene: 2.08 g and monoethanolamine to pH = 9.4 | dark red | Untreated hair: After the coloring: | +83.30; +21.93 | −0.48; +24.99; | +10.40 +3.41 | white |
| 2.4 | (A1) 1,2,3,3-tetramethyl-3H-indolium hydrogen sulfate: 3.12 g, pH = 1.7; (A2) N,N-dimethyl-4-(((2-hydroxyethyl)imino)methyl)aniline: 2.21 g without monoethanolamine pH 11.0 | intensive pinkish red | Untreated hair: After the coloring: | +83.30; +39.83 | −0.48; +67.33; | +10.40 +10.32 | white |
| 2.7 | (A1) 1,2,3,3-tetramethyl-3H-indolium hydrogen sulfate: 3.12 g, pH = 1.7; (A2) 1,2-dihydroxy-3-(((2-hydroxyethyl)imino)methyl)benzene: 2.08 g and monoethanolamine to pH = 9.6 | yellowish green | Untreated hair: After the coloring: | +83.30; +49.40 | −0.48; +3.10 | +10.40 +35.50 | white |
| 2.8 | (A1) 1,2,3,3-tetramethyl-3H-indolium hydrogen sulfate: 3.12 g, pH = 1.7; (A2) 4-(((3-hydroxypropyl)-imino)methyl)phenol: 2.06 g and monoethanolamine to pH 9.6 | intensive orange | Untreated hair: After the coloring: | +83.30; +49.99 | −0.48; +60.78; | +10.40 +53.05 | white |
| 2.9 | (A1) 1,2,3,3-tetramethyl-3H-indolium hydrogen sulfate: 3.12 g, pH = 1.7; (A2) 2,6-dimethoxy-4-(((3-hydroxypropyl)imino)methyl)phenol: 2.75 g and monoethanolamine to pH = 9.7 | intensive violet | Untreated hair: After the coloring: | +83.30; +20.87 | −0.48; +42.77; | +10.40 −1.23 | white |
| 2.10 | (A1) 1,2,3,3-tetramethyl-3H-indolium hydrogen sulfate: 3.12 g, pH = 1.7; (A2) 4-(((2,3-dihydroxypropyl)-imino)methyl)phenol: 2.25 g and monoethanolamine to pH 9.6 | intensive orange | Untreated hair: After the coloring: | +83.30; +50.66 | −0.48; +58.05; | +10.40 +55.55 | white |
| 2.11 | (A1) 1,2,3,3-tetramethyl-3H-indolium hydrogen sulfate: 3.12 g, pH = 1.7; (A2) 2,6-dimethoxy-4-(((2,3-dihydroxypropyl)imino)methyl)-phenol: 2.94 g and monoethanolamine to pH = 9.4 | intensive violet | Untreated hair After the coloring: | +83.30; +21.18 | −0.48; +40.69; | +10.40 +−2.99 | white |
| 2.12 | (A1) 1,2,3,3-tetramethyl-3H-indolium hydrogen sulfate: 3.12 g, pH = 1.7; (A2) 2-[(4-hydroxy-benzylidene)-amino]-propane-1,3-diol: 2.25 g and monoethanolamine to pH 9.7 | intensive orange | Untreated hair: After the coloring: | +83.30; +50.85 | −0.48; +56.67; | +10.40 +54.97 | white |
| 2.13 | (A1) 1,2,3,3-tetramethyl-3H-indolium hydrogen sulfate: 3.12 g, pH = 1.7; (A2) 2-[(4-hydroxy-3,5-dimethoxy-benzylidene)-amino]-propane-1,3-diol: 2.94 g and monoethanolamine to pH = 9.2 | intensive violet | Untreated hair: After the coloring: | +83.30; +22.21 | −0.48; +42.35; | +10.40 −1.60 | white |
| 2.14 | (A1) 1,2,3,3-tetramethyl-3H-indolium hydrogen sulfate: 3.12 g, pH = 1.7; (A2) 4-(((2-hydroxy-2-phenyl-ethyl)imino)methyl)phenol: 2.77 g and monoethanolamine to pH 9.6 | intensive orange | Untreated hair: After the coloring: | +83.30; +51.66 | −0.48; +55.67; | +10.40 +55.08 | white |

TABLE 1-continued

Color Results

| No. | Enamine of Formula (I), contained in Component (A1) Schiff's Base of Formula (II), contained in Component (A2) | Shade after the coloring | | Measured Color Values | | | Shade after decolorizing |
|---|---|---|---|---|---|---|---|
| | | | | L | a | b | |
| 2.15 | (A1) 1,2,3,3-tetramethyl-3H-indolium hydrogen sulfate: 3.12 g, pH = 1.7; (A2) 2,6-dimethoxy-4-(((l-phenyl-2-hydroxyethyl)imino)methyl)phenol: 3.47 g and monoethanolamine to pH = 9.5 | intensive violet | Untreated hair: After the coloring: | +83.30; +22.07 | −0.48; +39.20; | +10.40 +0.32 | white |
| 2.16 | (A1) 1,2,3,3-tetramethyl-3H-indolium hydrogen sulfate: 3.12 g, pH = 1.7; (A2) 4-(((2-hydroxyphenyl)-imino)methyl)phenol: 2.45 g and monoethanolamine to pH 8.9 | intensive orange | Untreated hair: After the coloring: | +83.30; +49.11 | −0.48; +56.69; | +10.40 +54.91 | white |
| 2.17 | (A1) 1,2,3,3-tetramethyl-3H-indolium hydrogen sulfate: 3.12 g, pH = 1.7; (A2) 2,6-dimethoxy-4-(((2-hydroxyphenyl)imino)methyl)phenol: 3.14 g and monoethanolamine to pH = 9.5 | intensive violet | Untreated hair: After the coloring: | +83.30; +20.95 | −0.48; +34.57; | +10.40 +0.68 | white |
| 2.18 | (A1) 1,2,3,3-tetramethyl-3H-indolium hydrogen sulfate: 3.12 g, pH = 1.7; (A2) 5-guanidino-2-[(4-hydroxy-benzylidene)amino]-pentanoic acid: 3.20 g and monoethanolamine to pH 9.5 | intensive orange | Untreated hair: After the coloring: | +83.30; +52.97 | −0.48; +55.56; | +10.40 +58.45 | white |
| 2.19 | (A1) 1,2,3,3-tetramethyl-3H-indolium hydrogen sulfate: 3.12 g, pH = 1.7; (A2) 2-[(4-dimethylamino-naphthalene-1-ylmethylene)-amino]ethanol: 2.79 g and monoethanolamine to pH = 11.0 | intensive violet | Untreated hair: After the coloring: | +83.30; +35.40 | −0.48; +20.58; | +10.40 −15.69 | white |
| 2.20 | (A1) 5-hydroxy-1,2,3,3-tetramethyl-3H-indolium iodide: 3.65 g, pH = 3.7; (A2) 2-[(4-dimethylamino-naphthalene-1-ylmethylene)-amino]-ethanol: 2.79 g and monoethanolamine to pH 11.0 | intensive violet | Untreated hair: After the coloring: | +83.30; 36.34 | −0.48; 12.41; | +10.40 −8.50 | white |

What is claimed is:

1. A composition for coloring fibers (A), which is prepared by mixing two components (A1) and (A2), wherein component (A1) has an acidic pH and contains at least enamine of Formula (I) or its acid addition salt of Formula (Ia),

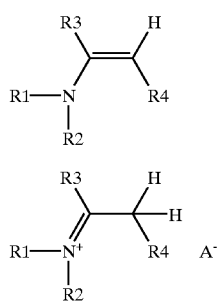

wherein $R_1$ represents a single ring or multi-ring aromatic group, an unsubstituted 5-membered or 6-membered heterocyclic group, a 5-membered or 6-membered aryl group, substituted with a C1 to C4 alkyl group, a C1 to C4 hydroxyalkyl group, a hydroxy group, a methoxy group, a dialkylamino group or a halogen group, or a 5-membered or 6-membered heterocyclic group, substituted with a C1 to C4 alkyl group, a C1 to C4 hydroxyalkyl group, a hydroxy group, a methoxy group, a dialkylamino group or a halogen group, $R_2$ is a linear or branched C1 to C8 alkyl group or a linear or branched C1 to C8 hydroxyalkyl group, a C1 to C8 alkoxyalkyl group, wherein oxygen atoms may be located between the carbon atoms of the alkyl chain, $R_3$ is a linear or branched C1 to C8 alkyl group, a C1 to C8 alkoxyalkyl group, a linear or branched C1 to C8 alkylene group, a C1 to C8 alkoxyalkylene group, an oxygen atom, a sulfur atom, an —NH group, or an —NR group, wherein R is an alkyl group, an alkoxyalkyl group, a hydroxyalkyl group or hydrogen, the $R_1$ and $R_3$ groups, together with the nitrogen atom and the carbon atom of the basic enamine structure being able to form a cyclic compound and $R_4$ being hydrogen, a linear C1 to C4 alkyl group or a branched C1 to C4 alkyl group, $A^-$ being the anion of an organic or inorganic acid, and the component (A2) having an alkaline pH and containing at least one Schiff's base of Formula (II)

$$R_7HC=NR_8 \qquad (II)$$

wherein R7 is a group of the following formulas

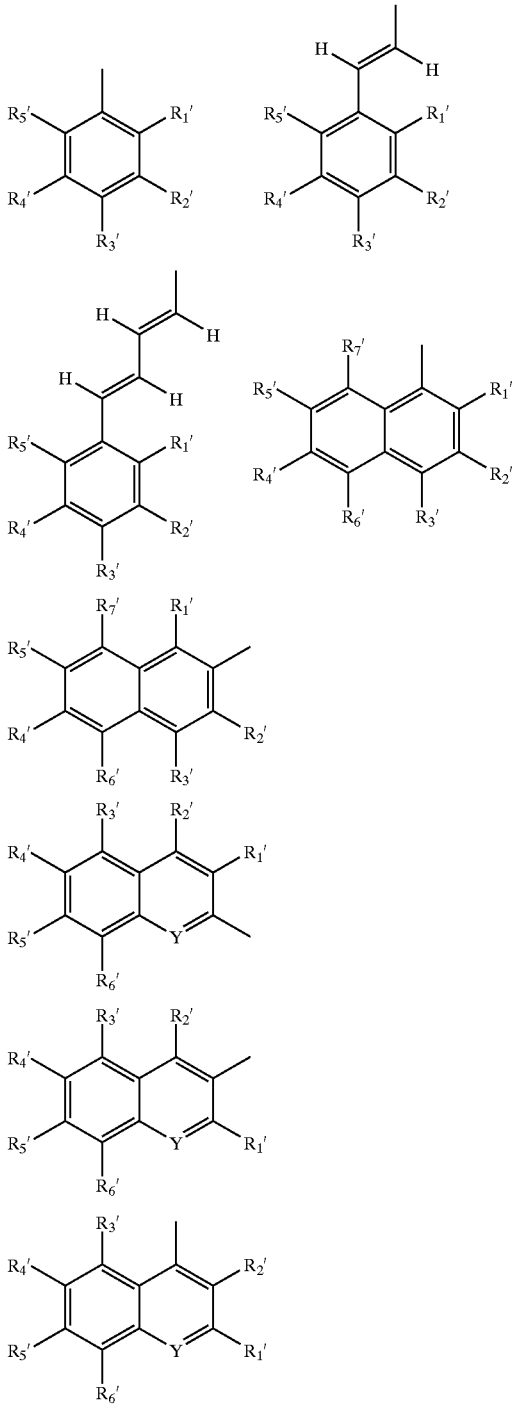

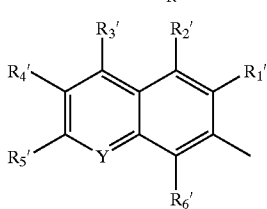

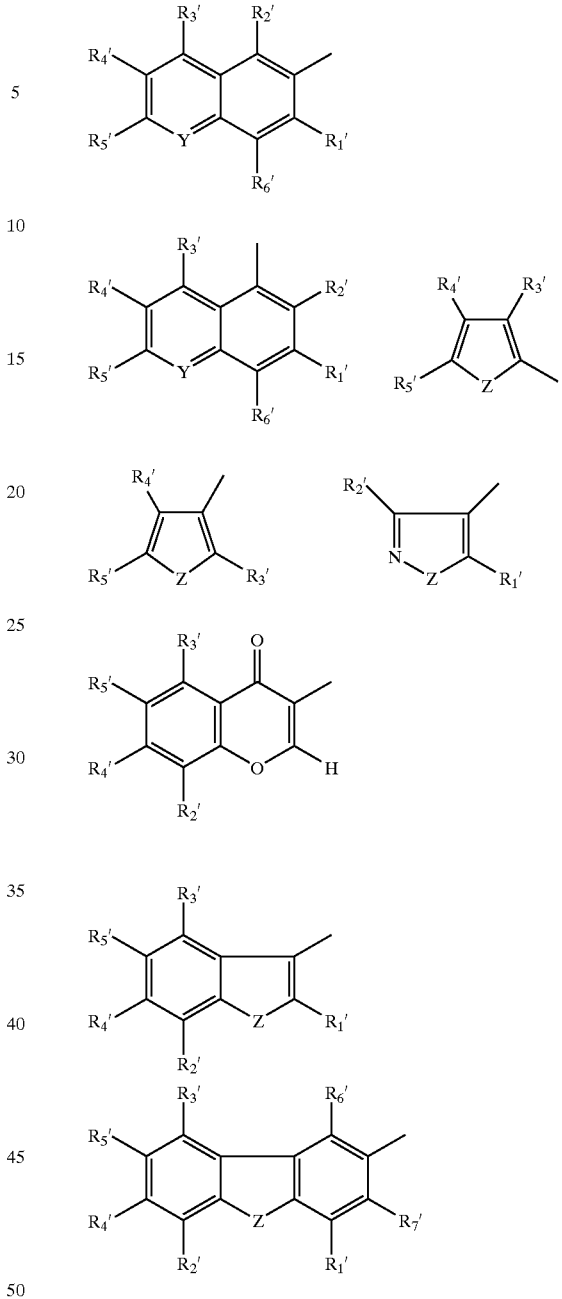

wherein Y and Z in each case are an oxygen atom, a sulfur atom or an $NR^a$ group, R1', R2', R3', R4', R5', R6' and R7' independently of one another are a hydrogen atom, a hydroxyl group, a methoxy group, an aryl group, a halogen atom, a —CHO group, a —$COR^a$ group, a —$CO_2R^a$ group, an —$NO_2$ group, an —$OCOR^a$ group, an —$OCH_2$ aryl group, an —$NH_2$ group, an —$NH_3^+$ group, an —$NHR^a$ group, an —$NR^aH_2^+$ group, an —$N(R^a)_2$ group, an —$N(R^a)_3^+$ group, an —$NHCOR^a$ group, an —$NHCOOR^a$ group, in which $R^a$ represents a hydrogen atom, a linear or branched C1 to C4 alkyl group, an optionally substituted aromatic carbon ring or heterocyclic ring, with the proviso that at least one of the R1' to R7' groups is not hydrogen, and R8 is a group of the following formulas

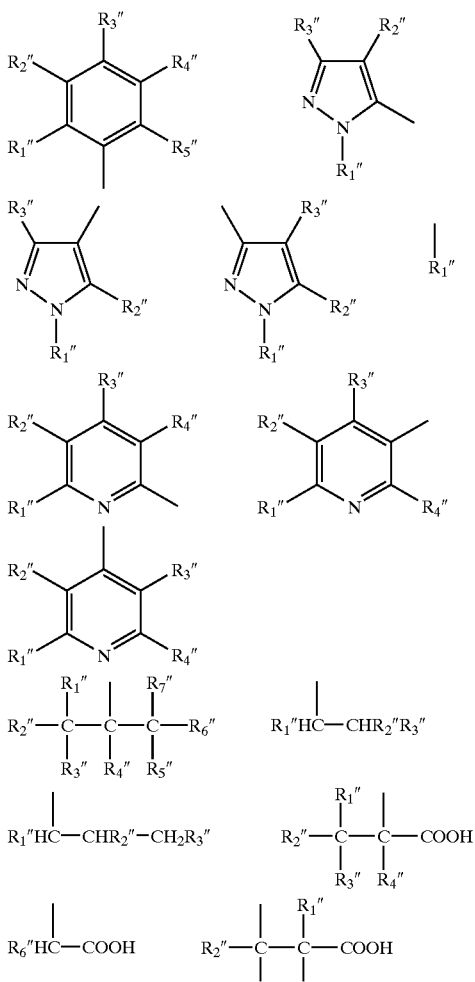

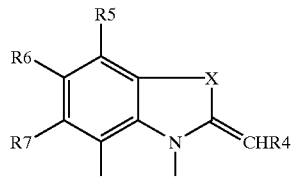

(IV)

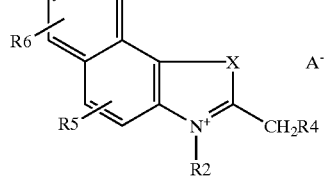

(V)

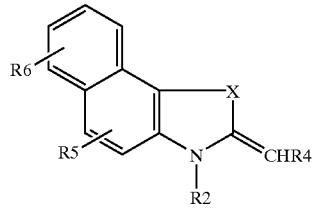

(VI)

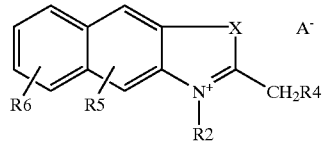

(VII)

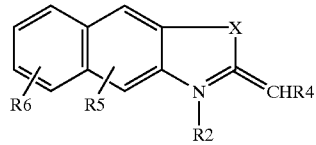

(VIII)

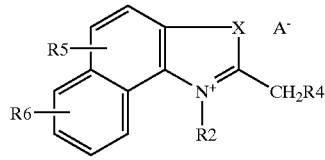

(IX)

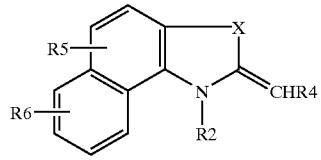

(X)

wherein R1", R2", R3", R4", R5", R6" and R7" independently of one another are a hydrogen atom, a methyl group, a halogen atom, a hydroxy group, a C1 to C4 hydroxyalkyl group, a benzyl group, an optionally substituted aromatic carbon ring or heterocyclic ring, a methoxy group, an ethoxy group, a carboxy group, an —NH₂ group, an —NHR$^b$ group, an —N(R$^b$)₂ group, in which R$^b$ is a hydrogen atom, a linear or branched C1 to C4 alkyl group, a C1 to C4 hydroxyalkyl group, an optionally substituted aromatic carbon ring or an optionally substituted aromatic heterocyclic ring and R8" is a group, required to form a natural α-amino acid.

2. The preparation of claim 1, wherein the compound of Formula (I) is selected from enamines of Formulas (III) to (X), (III)

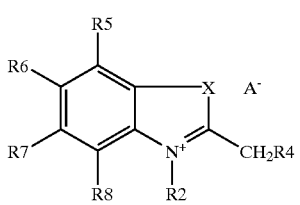

in which X is a carbon atom, substituted with two C1 to C4 alkyl groups, which may be the same or different and, in particular, a carbon atom, substituted with a C1 to C4 alkyl group and a hydroxyl group, a sulfur atom, an alkylated nitrogen atom, a not-alkylated nitrogen atom or an oxygen atom, and R2 is a linear or branched C1 to C8 alkyl group, a linear or branched C1 to C8 hydroxyalkyl group, or a C1 to C8 alkoxyalkyl group, in which there may be oxygen atoms between the carbon atoms of the alkyl chain, R4 is hydrogen, a linear C1 to C4 alkyl group or a branched C1 to C4 alkyl group, R5, R6, R7 and R8 independently of one another are hydrogen, a linear or branched C1 to C4 alkyl group, a linear or branched C1 to C4 hydroxyalkyl group, a hydroxy group, a methoxy group, an amino group, a monoalkylamino group, a dialkylamino group, a benzyl group or a halogen atom and A⁻ is chloride, bromide, iodide, sulfate, hydrogen sulfate, toluenesulfonate, benzenesulfonate, monomethyl sulfate, hexafluorophosphate, hexafluoroantimonate, tetrafluoroborate, tetraphenylborate, formate, acetate or propionate.

3. The preparation of claims 1 or 2, wherein the compound of Formulas (I) and (III) to (X) is selected from 1,3,3-trimethyl-2-methylene-indoline as well as its salts, 1,3,3,4-tetramethyl-2-methylene-indoline as well as its salts, 1,3,3,5-tetramethyl-2-methylene-indoline as well as its salts, 1,3,3,6-tetramethyl-2-methylene-indoline as well as its salts, 1,3,3,7-tetramethyl-2-methylene-indoline as well as its salts, 1,3,3,6,7-pentamethyl-2-methylene-indoline as well as its salts, 1,3,3,5,7-pentamethyl-2-methylene-indoline as well as its salts, 1,3,3,4,7-pentamethyl-2-methylene-indoline as well as its salts, 5-chloro-1,3,3-trimethyl-2-methylene-indoline as well as its salts, 5-fluoro-1,3,3-trimethyl-2-methylene-indoline as well as its salts, 5-isopropyl-1,3,3-trimethyl-2-methylene-indoline as well as its salts, 5-hydroxy-1,3,3-trimethyl-2-methylene-indoline as well as its salts, 5-methoxy-1,3,3-trimethyl-2-methylene-indoline as well as its salts, 5-amino-1,3,3-trimethyl-2-methylene-indoline as well as its salts, 5-N-acetylamino-1,3,3-trimethyl-2-methylene-indoline as well as its salts, 5-methoxy-6-N-acetylamino-1,3,3-trimethyl-2-methylene-indoline as well as its salts, 5-hydroxy-7-N-acetylamino-1,3,3-trimethyl-2-methylene-indoline as well as its salts, 6-hydroxy-1,3,3-trimethyl-2-methylene-indoline as well as its salts, 6-methoxy-1,3,3-trimethyl-2-methylene-indoline as well as its salts, 5-methoxy-6-amino-1,3,3-trimethyl-2-methylene-indoline as well as its salts, 5,6-dihydroxy-1,3,3-trimethyl-2-methylene-indoline as well as its salts, 5,6-dimethoxy-1,3,3-trimethyl-2-methylene-indoline as well as its salts, 4,5-dihydroxy-1,3,3-trimethyl-2-methylene-indoline as well as its salts, 5,7-dihydroxy-1,3,3-trimethyl-2-methylene-indoline as well as its salts, 5-amino-6-methoxy-1,3,3-trimethyl-2-methylene-indoline as well as its salts, 5-amino-7-hydroxy-1,3,3-trimethyl-2-methylene-indoline as well as its salts, 5-hydroxy-7-amino-1,3,3-trimethyl-2-methylene-indoline as well as its salts, 1-(2'-hydroxyethyl)-3,3-dimethyl-2-methylene-indoline as well as its salts, 1,3,3-trimethyl-2-methylene-3H-benz[e]indole as well as its salts and N-ethyl-2-methylene-benzthiazole as well as its salts.

4. The preparation of one of the claims 1 to 3, wherein the Schiff's base of Formula (II) is selected from
4-(((2-hydroxyethyl)imino)methyl)-2-methoxyphenol,
5-(((2-hydroxyethyl)imino)methyl)-2-methoxyphenol,
2,6-dimethoxy-4-(((2-hydroxyethyl)imino)methyl)phenol,
4-(((2-hydroxyethyl)imino)methyl)phenol,
1,2-dihydroxy-4-(((2-hydroxyethyl)imino)methyl)benzene,
N,N-dimethyl-4-(((2-hydroxyethyl)imino)methyl)-aniline,
1,2-dihydroxy-3-(((2-hydroxyethyl)imino)methyl)benzene,
4-(((3-hydroxypropyl)imino)methyl)phenol,
2,6-dimethoxy-4-(((3-hydroxypropyl)imino)methyl)phenol,
4-(((2,3-dihydroxypropyl)imino)methyl)phenol,
2,6-dimethoxy-4-(((2,3-dihydroxypropyl)imino)methyl)phenol,
2-[(4-hydroxy-benzylidene)-amino]-propane-1,3-diol,
2-[(4-hydroxy-3,5-dimethoxy-benzylidene)-amino]-propane-1,3-diol,
4-(((2-hydroxy-2-phenyl-ethyl)imino)methyl)phenol,
2,6-dimethoxy-4-(((1-phenyl-2-hydroxy-ethyl)imino)methyl)phenol,
4-(((2-hydroxyphenyl)imino)methyl)phenol,
2,6-dimethoxy-4-(((2-hydroxyphenyl)imino)methyl)phenol,
5-guanidino-2-[(4-hydroxy-benzylidene)-amino]-pentanoic acid,
2-[(4-dimethylamino-naphthalene-1-ylmethylene)-amino]-ethanol,
5-guanidino-2-[(4-hydroxy-3,5-dimethoxy-benzylidene)-amino]-pentanoic acid, 2-[(4-hydroxy-3,5-dimethoxy-benzylidene)-amino]-3-(3H-imidazole-4-yl)-propanoic acid, 2-[(4-hydroxy-benzylidene)-amino]-3-(3H-imidazole-4-yl)-propanoic acid, 2-[(4-hydroxy-3,5-dimethoxy-benzylidene)-amino]-3-(1H-indole-3-yl)-propanoic acid, 2-[(4-hydroxy-benzylidene)-amino]-3-(1H-indole-3-yl)-propanoic acid, 2-(((2-hydroxyethyl)imino)methyl)phenol, 1,2-dihydroxy-3-(((2-hydroxyethyl)imino)methyl)benzene, 1,2,3-trihydroxy-4-(((2-hydroxy-ethyl)imino)methyl)benzene, 1,2,3,4-tetrahydroxy-5-(((2-hydroxyethyl)-imino)methyl)benzene and 1,2,4-trihydroxy-4-(((2-hydroxyethyl)imino)-methyl)benzene.

5. The preparation of one of the claims 1 to 4, wherein component (A1) has a pH of 1 to 4.5.

6. The preparation of one of the claims 1 to 5, wherein component (A2) has a pH of 7.5 to 12.

7. The preparation of one of the claims 1 to 6, wherein the enamine of Formula (I) or (III) to (X), as well as the Schiff's base of Formula (II), are in each case contained in a total amount of 0.01 to 10% by weight based on the ready-for-use preparation.

8. The preparation of one of the claims 1 to 7, wherein components (A1) and (A2) are present in the form of a solution, an emulsion, a foam, a cream, a gel, a powder, a granulate or an effervescent tablet.

9. A method for temporarily coloring fibers, especially hair, for which the fibers are colored with a preparation of one of the claims 1 to 8 and decolorized once again at any later time, wherein a sulfite-containing preparation is allowed to act on the colored fibers for a period of 5 to 60 minutes at a temperature of 20° C. to 50° C. for the purpose of decolorizing them.

10. A multi-component kit, comprising a component (A1), containing an enamine of Formula (I)/(Ia) of claim 1 and a component (A2), containing a Schiff's base of Formula (II) of claim 1.

* * * * *